(12) United States Patent
Alkhatib

(10) Patent No.: US 8,795,346 B2
(45) Date of Patent: Aug. 5, 2014

(54) SEMI RIGID EDGE PROTECTION DESIGN FOR STENT DELIVERY SYSTEM

(75) Inventor: Yousef Alkhatib, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1508 days.

(21) Appl. No.: 11/601,903

(22) Filed: Nov. 20, 2006

(65) Prior Publication Data

US 2008/0119922 A1    May 22, 2008

(51) Int. Cl.
- A61F 2/06 (2013.01)
- A61F 2/958 (2013.01)
- A61F 2/95 (2013.01)

(52) U.S. Cl.
CPC ......... *A61F 2/958* (2013.01); *A61F 2002/9586* (2013.01); *A61F 2002/9528* (2013.01)
USPC ....................................................... 623/1.11

(58) Field of Classification Search
USPC .................. 623/1.11; 606/190–195; 604/103, 604/103.07, 509, 95.03, 96.01, 97.01, 604/101.01–101.05, 912, 915
See application file for complete search history.

(56) References Cited

U.S. PATENT DOCUMENTS

| | | | | |
|---|---|---|---|---|
| 4,893,623 A * | 1/1990 | Rosenbluth | ................... | 606/192 |
| 4,976,720 A * | 12/1990 | Machold et al. | ............... | 606/194 |
| 4,998,923 A * | 3/1991 | Samson et al. | ................. | 606/194 |
| 5,328,468 A * | 7/1994 | Kaneko et al. | ............ | 604/103.13 |
| 5,378,236 A * | 1/1995 | Seifert | ....................... | 604/99.04 |
| 5,380,282 A * | 1/1995 | Burns | ........................ | 604/99.04 |
| 5,759,191 A * | 6/1998 | Barbere | ........................ | 606/194 |
| 5,769,814 A * | 6/1998 | Wijay | ........................ | 604/103.1 |
| 5,968,069 A | 10/1999 | Dusbabek et al. | ............ | 606/194 |
| 6,050,972 A * | 4/2000 | Zadno-Azizi et al. | ....... | 604/97.01 |
| 6,077,273 A | 6/2000 | Euteneuer | | |
| 6,139,525 A * | 10/2000 | Davis-Lemessy et al. | ... | 604/103 |
| 6,289,568 B1 * | 9/2001 | Miller et al. | ..................... | 29/423 |
| 6,589,274 B2 * | 7/2003 | Stiger et al. | ................... | 623/1.11 |
| 6,702,802 B1 * | 3/2004 | Hancock et al. | ............... | 604/524 |
| 2001/0000350 A1 * | 4/2001 | Durcan et al. | ............... | 623/1.11 |
| 2001/0007082 A1 * | 7/2001 | Dusbabek et al. | ........... | 623/1.11 |
| 2001/0014821 A1 * | 8/2001 | Juman et al. | ................. | 623/1.11 |
| 2001/0044630 A1 * | 11/2001 | Stack et al. | ..................... | 606/108 |
| 2002/0007102 A1 * | 1/2002 | Salmon et al. | .................... | 600/3 |
| 2002/0016564 A1 * | 2/2002 | Courtney et al. | .......... | 604/96.01 |
| 2003/0074016 A1 | 4/2003 | Campbell | | |
| 2003/0105508 A1 | 6/2003 | Johnson et al. | ............... | 623/1.11 |
| 2004/0102791 A1 * | 5/2004 | Murray, III | ................... | 606/108 |
| 2004/0260379 A1 | 12/2004 | Jagger et al. | ................. | 623/1.11 |
| 2004/0267280 A1 | 12/2004 | Nishide | | |
| 2005/0149161 A1 | 7/2005 | Eidenschink et al. | ....... | 623/1.11 |

FOREIGN PATENT DOCUMENTS

| | | |
|---|---|---|
| EP | 1 132 059 B1 | 3/2001 |
| WO | 9721400 | 6/1997 |
| WO | 2004/047685 A1 | 6/2004 |
| WO | 2006104750 | 10/2006 |

\* cited by examiner

*Primary Examiner* — David Eastwood
(74) *Attorney, Agent, or Firm* — Vidas, Arrett & Steinkraus, P.A.

(57) ABSTRACT

A system to deliver or remove an inflation expandable stent in a body vessel. The system avoids causing damage or embolisms to a body vessel it is traversing by restraining the edges of the stent from scraping against the walls of the body vessel. The edges are restrained by balloon folds, compressive wedging, and angled reflective resistance. In addition the device can also inflate or deflate the balloon more efficiently.

13 Claims, 6 Drawing Sheets

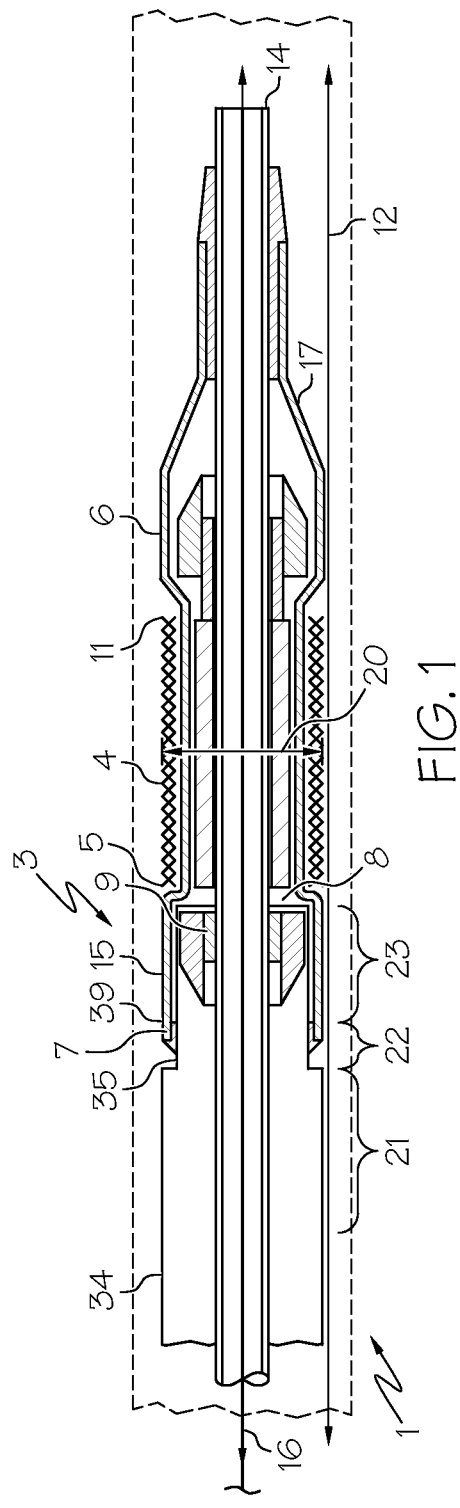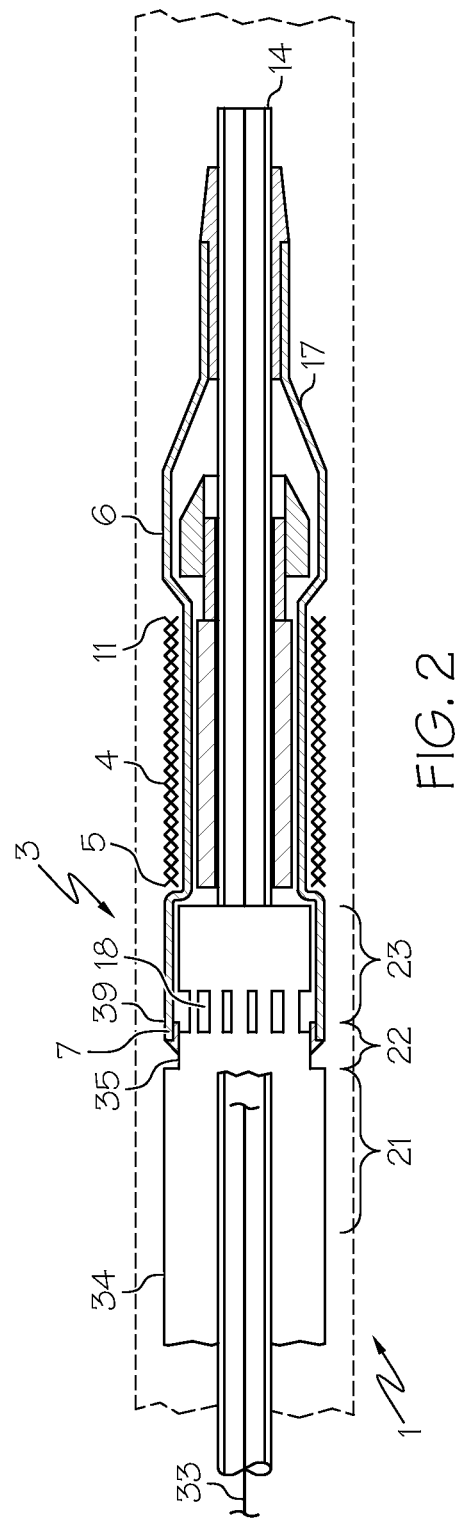

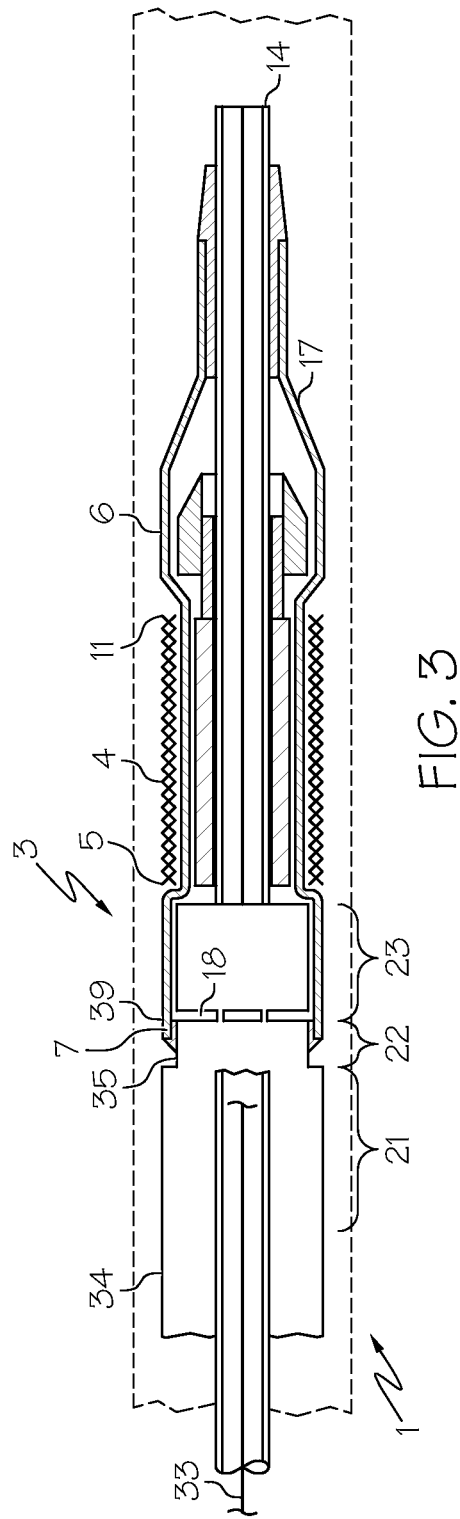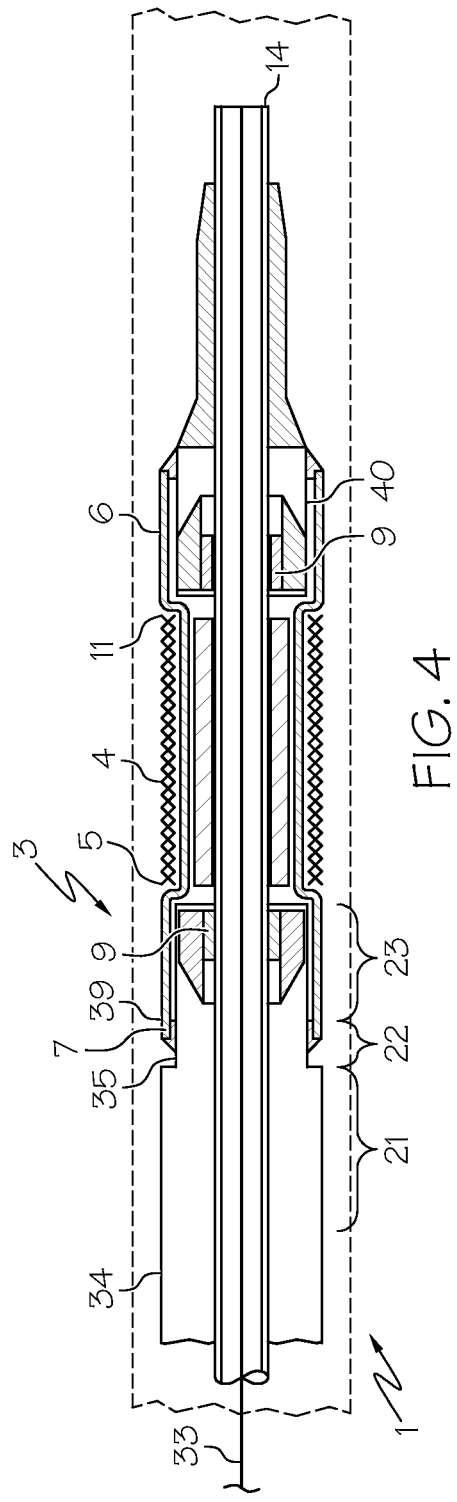

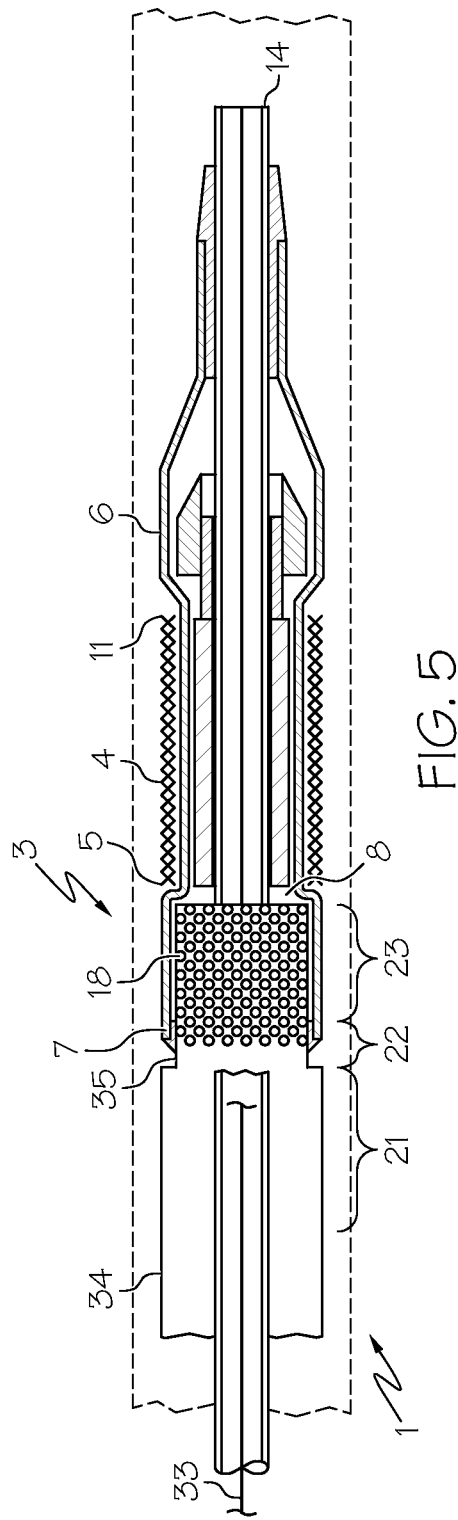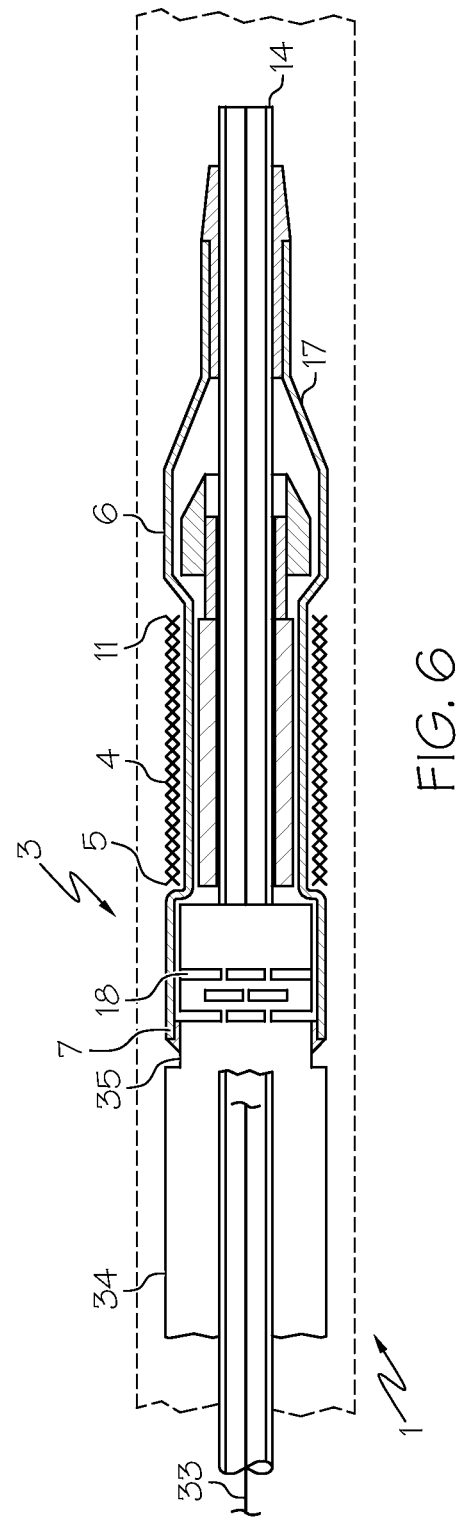

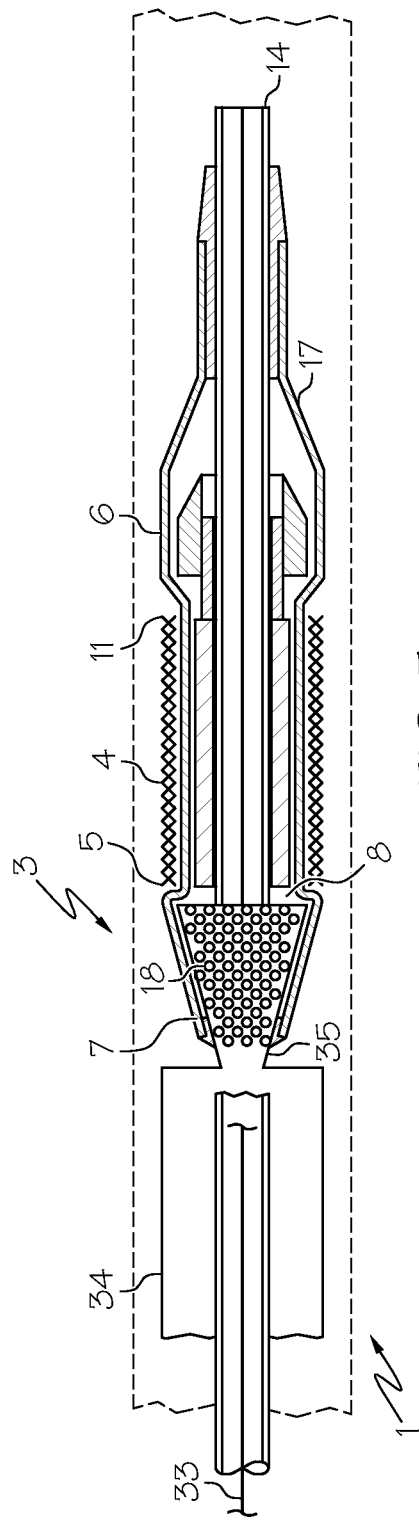
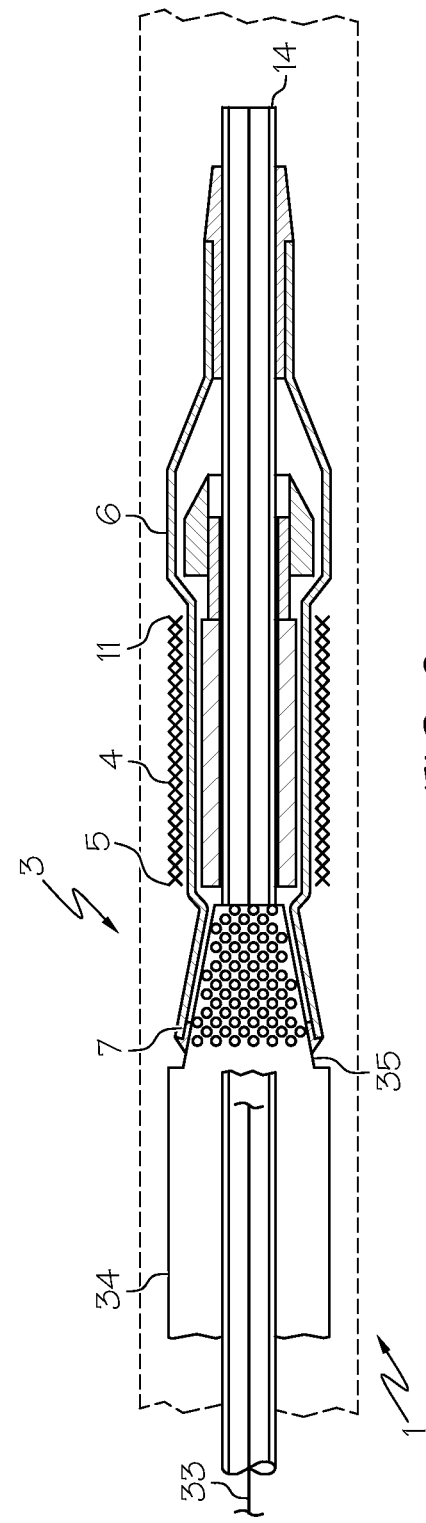

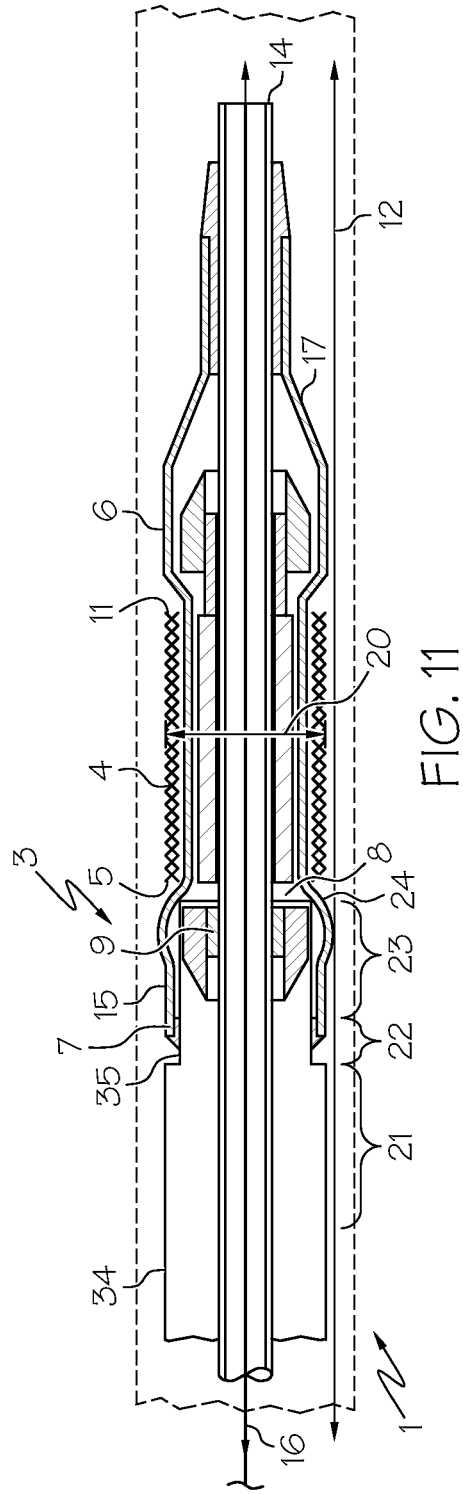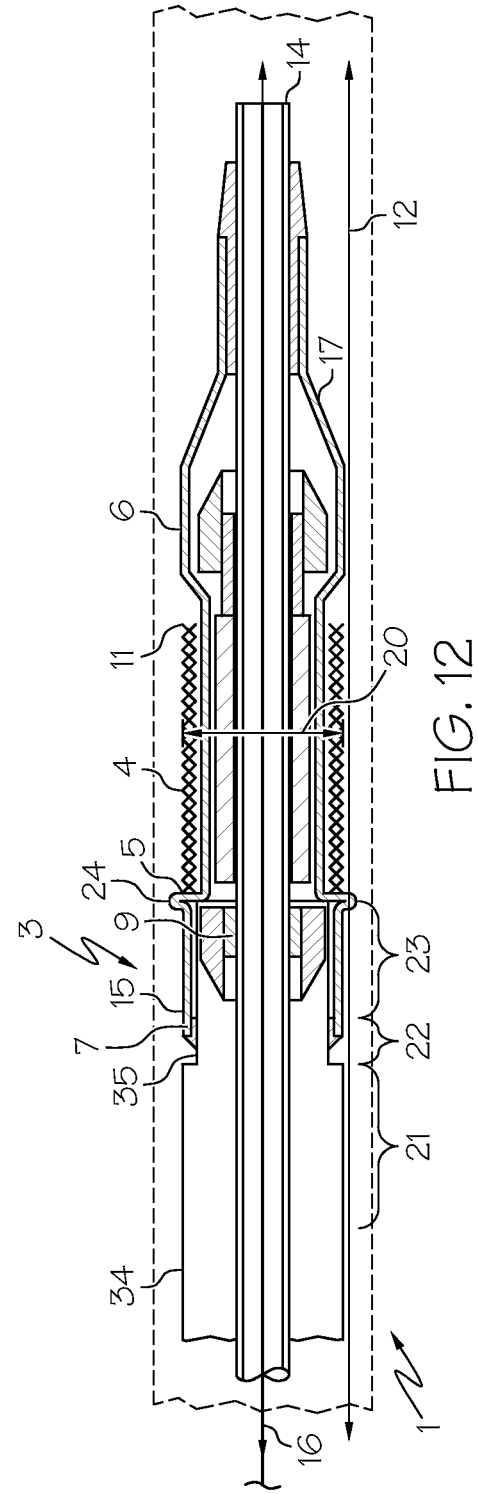

SEMI RIGID EDGE PROTECTION DESIGN FOR STENT DELIVERY SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. More particularly some embodiments of this invention relate to delivery systems for intravascular stents, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration is delivered by a stent delivery system or "SDS" to the site where it is required.

In some circumstances however, a stent or other medical device which is tracked through body vessels ultimately is not implanted and needs to be removed. Non-implantation may result from a number of causes including but not limited to lack of success in reaching the intended target lesion. When the stent will not be implanted its removal becomes necessary. Stent removal can involve both pulling the stent back in the opposite direction of its insertion as well as possibly pushing the stent further into a body vessel. The already tracked device at this point however could have experienced flexing which can cause flaring at one or more ends of the stent. This can result in the flared end(s) of the stent catching on portions of the body vessel upon further movement in either direction and thus cause embolization or vessel damage.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

Some embodiments of the invention are directed to features that can be incorporated into catheters in general, and particularly stent delivery systems (SDS) to facilitate proximal and distal (if desired) edge protection to the stent in the event of aborting stent delivery and/or deployment. This invention contemplates a number of embodiments where any one, any combination of some, or all of the embodiments can be incorporated into a stent delivery system and/or a method of use.

At least one of the embodiments of the inventive concept is directed to an SDS having an outer neck which extends distally into the balloon cone or distally into the balloon working region. The inventive concept also contemplates at least one embodiment directed to an SDS having a tapered outer neck. At least one embodiment encompassed by the inventive concept is directed to an SDS having one or more aperture extending through the side walls of the outer neck. In at least one embodiment these apertures facilitate the inflation or deflation of a balloon.

One or more embodiments of the inventive concept are directed to a second reinforcing member located at the distal end of the SDS which protrudes into the distal cone of the balloon, protrudes into the distal side of the working region of the balloon, has one or more inflating or deflating apertures, has a tapered shape, or any combination thereof.

BRIEF DESCRIPTION OF THE SEVERAL VIEWS OF THE DRAWINGS

The invention is best understood from the following detailed description when read in connection with accompanying drawings, in which:

FIG. 1 is an image of a Stent Delivery System (SDS) in which the region immediately proximal to the crimped stent has been edge protected to facilitate easy removal from a body vessel.

FIG. 2 is an image of an SDS in which the region immediately proximal to the crimped stent has been edge protected and has longitudinal slots.

FIG. 3 is an image of an SDS in which the region immediately proximal to the crimped stent has been edge protected and the outer lumen has circumferential slots.

FIG. 4 is an image of an SDS in which both the region immediately proximal to the crimped stent and the region immediately distal to the crimped stent have been edge protected.

FIG. 5 is an image of an SDS in which the region immediately proximal to the crimped stent has been edge protected and the outer lumen has a plurality of apertures.

FIG. 6 is an image of an SDS in which the region immediately proximal to the crimped stent has been edge protected and the outer lumen has a plurality of longitudinally displaced slots.

FIG. 7 is an image of an SDS in which the region immediately proximal to the crimped stent has been edge protected, the outer lumen has a plurality of apertures, and the outer lumen has a distally widened conical shape.

FIG. 8 is an image of an SDS in which the region immediately proximal to the crimped stent has been edge protected, the outer lumen has a plurality of apertures, and the outer lumen has a proximally widened conical shape.

FIG. 11 is an image of an SDS with an outwardly protruding balloon.

FIG. 12 is an image of an SDS with an outwardly folded balloon.

DETAILED DESCRIPTION OF THE INVENTION

Figure 9:
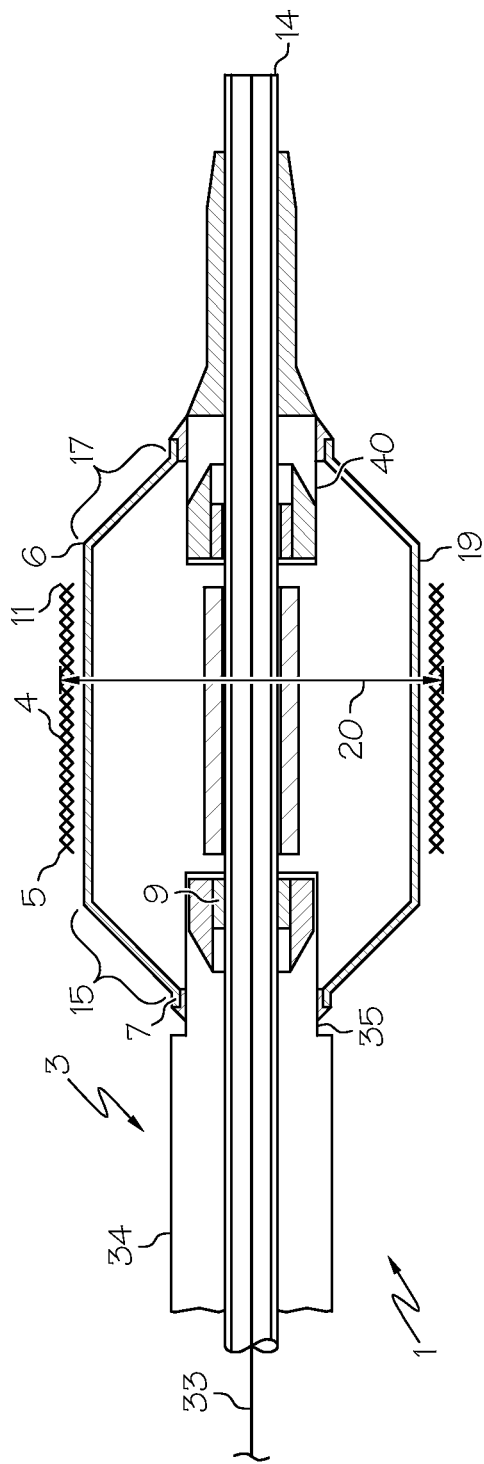
FIG. 9 is an image of an SDS after the balloon has been inflated in which both the region immediately proximal to the crimped stent and the region immediately distal to the crimped stent have been edge protected.

The invention will next be illustrated with reference to the figures wherein the same numbers indicate similar elements in all figures. Such figures are intended to be illustrative rather than limiting and are included herewith to facilitate the explanation of the apparatus of the present invention. For the purposes of this disclosure, like reference numerals in the figures shall refer to like features unless otherwise indicated. Depicted in the figures are various aspects of the invention. Elements depicted in one figure may be combined with, or substituted for, elements depicted in another figure as desired.

Referring now to FIG. 1 there is shown a stent delivery system (SDS) (1) in an unexpanded configuration. The SDS (1) comprises an unexpanded stent (4) crimped about a catheter or shaft (3). The stent (4) has a proximal edge (5) and a distal edge (11) and is constructed to have a tubular structure with a diameter (20). The diameter (20) has a first magnitude which permits intraluminal delivery of the tubular structure into the body vessel passageway, and a second expanded and/or deformed magnitude (as shown in FIG. 9) which is achieved upon the application of a radially, outwardly expanding force.

The SDS (1) also comprises an outer tube or shaft (34) which defines an outer lumen. Within the outer tube (34) is a portion of an inner tube (14). The inner tube (14) defines an inner lumen. A portion of the inner tube (14) extends beyond the outer tube (34) and the crimped stent (4) is disposed about at least a portion of the inner tube (14). Sandwiched between the stent (4) and the portion of the inner tube (14) extending out of the outer tube (34) is a portion of an expansion balloon (6). The expansion balloon (6) extends longitudinally beyond both edges (5, 11) of the stent (4) and is functionally engaged to both the outer tube (34) and the inner tube (14) forming a substantially fluid tight seal between the outer and inner lumens. The portion of the balloon (6) engaged to the outer tube (34) is the waist (7) of the balloon. At times, positioned at or near the longitudinal position on the SDS (1) adjacent to the proximal end of either the balloon (6) or the stent (4) are one or more marker bands (9). The marker band (9) can contain a radiopaque material used for following the progress of the SDS (1) through the body vessel and/or can be used to block off unwanted longitudinal movement of the stent (4) along the catheter (3). Although FIGS. 1-12 illustrate the marker bands (9) as cylindrically trapezoidal, it is contemplated by the inventive concept that they be rectangular or in any other shape.

The SDS (1) of FIG. 1 is shown in its expanded state in FIG. 9. During a stent implantation, the SDS (1) is positioned adjacent to an implantation site of a body vessel and fluid is injected through the outer lumen (34) into the balloon (6). The injected fluid causes the balloon (6) to radially expand. A balloon (6) will typically have a proximal end region (15), a distal end region (17) and a working region (19) extending between the proximal end (15) and distal end (17) regions. As the balloon (6) expands, the working region (19) in turn expands the stent (4) which when fully expanded to the second magnitude diameter (20), is then implanted at the implantation site.

In at least one embodiment, the proximal and distal end regions (15, 17) are respectively proximal and distal cones (15, 17). The proximal and distal cones (15, 17) comprise those portions of the balloon (6) which longitudinally spans from the waist (7) to a portion of the working region (19) which is both closest to the waist (7) and most distant from the inner lumen (14) when in the second expanded state. The cones (15, 17) are so named because when expanded, those portions of the balloon (6) progressively expand away from the catheter (3) in a tapered or conical manner.

On some occasions however, the stent implantation will be aborted and the stent (4) must be removed from either the implantation site or from whichever body vessel the SDS (1) has tracked the stent (4) within. FIG. 1 illustrates at least one embodiment of the present invention where the end (5) of the stent (4) is reinforced by the extension of the outer neck (35) to a position considerably within the proximal balloon cone (15). The outer neck (35) comprises a portion of the outer tube (34) immediately proximal to the crimped stent (4). The outer neck (35) has two regions, a second region (22) and a third region (23) which is distal to the second region (22). The outer neck (35) is engaged to the balloon waist (7) at the second region (22). Both regions of the outer neck (35) are narrower than the main portion or first region (21) of the outer tube (34).

As illustrated in FIG. 1, the protrusion of the outer neck (35) into the balloon cone (15) provides reinforcement to the SDS (1) by limiting the flexibility of the unexpanded balloon (6). This decrease in balloon (6) flexibility reduces the amount the stent (4) can be bent when being tracked in any direction through body vessels while disposed about the balloon (6). By reducing the amount that the stent (4) can bend, it becomes less likely that the ends (5, 11) of the stent (4) will flex and flare outwards and snag or catch onto a wall of a body vessel and potentially cause damage or embolization. The reinforcement also makes it less likely that compressive forces encountered while tracking the SDS (1) through body vessels would deform the balloon and prevent proper inflation The protrusion of the outer neck (35) into the cone (15) has other benefits as well. The reinforcement provided by the protrusion, helps the SDS (1) resist bending in response to torque from levering forces applied along the length of the SDS (1) by movements of the mass at the end of the guide tip (29). By reducing bending of the SDS (1), misaligning of the balloon (6) and increased the flaring of the stent (4) is avoided. In addition, the protrusion of the outer neck (35) into the cone (15) also facilitates balloon (6) inflation. This is because the inflating fluid fed into the balloon (6) exits the third region (23) much closer to the working region (19) of the balloon preventing excessive accumulation of fluid in the cone (15) and providing more inflating pressure against the working region (19). The protrusion also protects the balloon material while it is folded onto the SDS (1) and while the stent (4) is crimped to the SDS (1). Lastly, the reinforcement makes the balloon (6) better able to avoid deformation in response to interacting with the force of the impact between the expanding stent (4) and the walls of the body vessel at the site of the stenosis.

There are a number of embodiments according to which the outer neck (35) can protrude into the cones (15). In at least one embodiment as shown in FIG. 4, the outer neck (35) extends radially past the marker band (9). In at least one embodiment, the outer neck (35) extends longitudinally past the marker band (9) to a position longitudinally closer to the stent (94). Alternatively the marker band (9) can be closer to the stent than the outer neck (35). In at least one embodiment as shown in FIGS. 4 and 9 a second reinforcing member (40) analogous to the protruding outer neck (35) can also be positioned adjacent to the distal end of the stent (11) and protrude into the distal cone (17) providing similar reinforcing properties at the distal end of the SDS (1).

In at least one embodiment as illustrated in FIG. 12, the outer neck (35) can longitudinally protrude so far into (or past) the cone (15) that it longitudinally extends to a position substantially flush with the edge of the stent (4). In at least one embodiment, the flush positioning causes a balloon bulge (24) to abut the stent end (5) which extends further radially than the stent end (5). This more radial extension causes the bulge (24) to block any radially vectored impacts or interactions between the stent edge (5) and body vessels. In addition, positioning the outer neck (35) almost flush against the stent end (5) can wedge the stent (4) into place and pinion the stent to resist any outward flaring caused by torque being applied to the stent (4).

Figure 10:
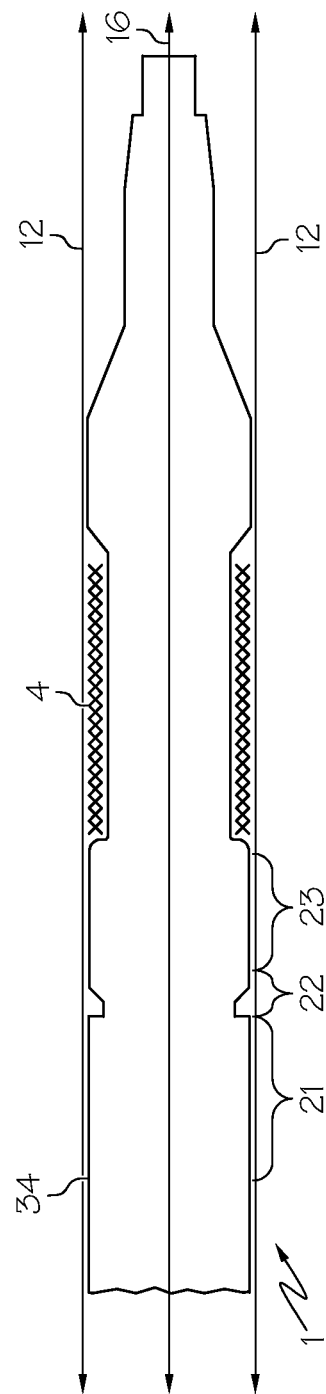
FIG. 10 is an image of an SDS with a common circumferential surface.

Referring now to FIG. 10 there is shown at least one embodiment of the inventive concept directed to an SDS (1) which can remove a non-implanted stent (4). In this SDS (1), the main portion (21) of the outer tube (34), the balloon waist (7) about the second region (22), and the crimped stent (4) are all sized such that their outer surfaces share a substantially similar circumference (12) relative to an axis (16) extending longitudinally through the center of the SDS (1). This common circumference (12) provides the SDS (1) a generally uniform surface facing the body vessel the SDS is tracked through. This uniform surface limits the likelihood of a portion of the SDS (1) becoming snagged against a portion of the body vessel whether the SDS is being moved in a proximal or distal direction.

As shown in FIG. 1, the inventive concept also contemplates at least one embodiment in which a gap (8) between the proximal edge (5) of the stent (4) and the distal end of the third region (23) of the outer neck (35) helps protects against harmful contact between the SDS (1) and a body vessel it is being tracked through. Within this gap (8), the material of the balloon (6) flows radially and longitudinally outward from beneath the stent (4) to a position outside of the outer neck (35). The folded balloon material within the gap will have a diameter smaller than that of the stent (4). This outward flowing balloon material wraps a portion of the balloon (6) around the proximal edge (5) of the stent (4) reducing the exposure of any irregular surface of the stent edge (5) to the body vessel the SDS (1) is being tracked through.

The gap (8) is properly spaced to accommodate balloon materials of a specific thickness such that the outer surface of the balloon (6) curves or arcs along an optimal path. In at least one embodiment illustrated in FIG. 1, the balloon material curves out from beneath the stent (4) to a position which is substantially flush and smooth with the common circumferential perimeter (12) without any bulging of either the stent (4) or the balloon (6).

In at least one embodiment illustrated in FIG. 11, the gap (8) is spaced such that it causes the outer surface of the balloon (6) to have an outward bulge (24) which protrudes beyond the circumferential perimeter (12) of the stent (4). Because the outward bulge (24) protrudes further in a radial direction than the stent end (5), the bulge (24) prevents the stent end (5) from coming into contact with any of the body vessels when the SDS (1) impacts against body vessels it is being tracked through. As illustrated in FIG. 4, at least one embodiment of the inventive concept is directed to a distal gap (8) between the distal end of the stent (11) and the proximal side of a second reinforcing member (40). The inventive concept contemplates a distal gaps as that of FIG. 4 in which there is no bulge protruding further in a radial direction than the stent end (5) as well as a spaced distal gap (8) allowing for an arced bulge similar to that of FIG. 11 at the distal side of the stent (4).

Referring now to FIGS. 7 and 8 there is shown an SDS (1) with a tapered outer neck (35). As FIG. 7 shows, at least a portion of the outer neck is tapered or conically shaped with a wider proximal area. In the alternative as shown in FIG. 8, at least a portion of the outer neck (35) is tapered with a wider distal area. The inventive concept also contemplates non-linear outer necks (35) including but not limited to outer necks (35) which are arced, slanted, waved, irregularly shaped, or which have one or more angled portions between distal and proximal ends with substantially similar or the same circumferences, and any combination thereof. In at least one embodiment, the angling of the tapering in the outer neck (35) reinforces the stent edge(s) by being directed opposite to the flare causing flexing that the stent (1) encounters. In at least one embodiment, a second reinforcing member at the distal side of the SDS (1) is similarly tapered.

FIGS. 2, 3, 5, 6, 7, and 8 illustrate SDSs (1) in which there are one or more cavities or apertures (18) extending through the wall of the outer necks (35). Because these illustrations disclose details of at least the outer surface of the outer neck (35), they do not explicitly show the inner tube (14) or guide wire (33) passing through the outer neck (35). It would be clear however, to practitioners of ordinary skill in the art however that these illustrations disclose embodiments in which one, both, or none, of the guide wire (33) and the inner lumen (14) pass through the outer neck (35) of the outer tube (34). Similarly, the inventive concept contemplates embodiments in which the various apertures (18) of FIGS. 2, 3, 5, 6, 7, and 8 are also present on the distal side of the SDS (1) positioned on a second reinforcing member (such as (40) in FIG. 4) analogous to the outer neck (35).

Sometimes an SDS (1) having an already inflated or partially inflated balloon (6) needs to be removed. FIG. 2 illustrates at least one embodiment in which an SDS (1) has at least one aperture (18) through which the fluid which previously inflated the balloon (6) can be drained or suctioned through. These apertures (18) can be one or more rectangular slots (as shown in FIG. 2) as well as circles, ellipse, squares, or any other known shape in the art. Similarly the apertures 15 can have their opening extend in a longitudinal manner (as in FIG. 2), in a circumferential manner (as in FIG. 3), diagonally, or in any possible combination of longitudinal, diagonal, or circumferential extension.

The number of the apertures (18), their size, and their distribution across the outer neck (35) can vary depending on the desired rate of fluid flow. In at least one embodiment, at least one aperture (18) extends longitudinally across a majority of the length of the outer neck (35). Similarly, in at least one embodiment, at least one aperture (18) extends circumferentially across a majority of the circumference of the outer neck (35). Also, in at least one embodiment one or more of the apertures (18) have one way openings or valves which reduce or prevent fluid flow while the balloon (6) is either being inflated or deflated, but allows fluid flow when the balloon (6) is being respectively deflated or inflated. Embodiments in which the end of the aperture (18) facing the outer lumen may have a different width or circumference than the end of the aperture (18) on the outer surface of the outer neck (35) and/or of any point along the length of the aperture (18) between these two ends are contemplated by this inventive concept. In addition, embodiments in which the apertures (18) facilitate a balloon (18) to be inflated more rapidly or easily than to be deflated or vice versa are contemplated by this inventive concept.

The apertures (18) can be of particular utility during the deflation of a balloon (6). During deflation, because the apertures (18) are positioned within the cones (15, 17) they can directly drain or suction fluid from the cones (15, 17). This helps to remove fluid that otherwise does not drain well from the narrow confines of the proximal and distal tips of the cones (15, 17). The drainage or suction provided by the apertures combined with the drainage or suction that the distal end of the third region (23) applies to the working region (19) assures that fluid is effectively drained from all portions of the balloon (6).

In at least one embodiment, as illustrated in FIG. 3, at least one aperture (18) is positioned on the outer neck (35) longitudinally adjacent to the tip of the proximal cone (15) which is located at the waist-cone transition point (39). Because the tip of the cone (15) is so narrow it is a harder location to apply a suction force to and it retains fluid with a greater surface tension. The positioning of at least one aperture (18) at the waist-cone transition point (39) allows for targeted drainage from the tip of the cone. In at least one embodiment, there are at least two apertures located on opposite sides of the outer neck (35).

In some embodiments the stent, the SDS, or other portion of an assembly may include one or more areas, bands, coatings, members, etc. that is (are) detectable by imaging modalities such as X-Ray, MRI, ultrasound, etc. In some embodiments at least a portion of the coating of the stent and/or adjacent assembly is at least partially radiopaque.

In addition, any coating can also comprise a therapeutic agent, a drug, or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate. It will be appreciated that other types of coating substances, well known to those skilled in the art, can be applied to the stent as well.

In some embodiments at least a portion of the stent is configured to include one or more mechanisms for the delivery of a therapeutic agent. Often the agent will be in the form of a coating or another layer (or layers) of material placed on a surface region of the stent, which is adapted to be released at the site of the stent's implantation or areas adjacent thereto.

This completes the description of the preferred and alternate embodiments of the invention. The above disclosure is intended to be illustrative and not exhaustive. This description will suggest many variations and alternatives to one of ordinary skill in this art. The various elements shown in the individual figures and described above may be combined, substituted, or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claims below.

The invention claimed is:

1. A balloon catheter comprising:
a balloon, an inner tube, an outer tube, and a stent having a proximal annular end, the balloon having an unexpanded configuration and an expanded configuration;
the balloon having a proximal end region, a distal end region, and a working region extending therebetween, the working region having a diameter, in the expanded configuration the diameter being greater than in the unexpanded configuration, the stent crimped about at least a portion of the working region when the balloon is in the unexpanded configuration;
the outer tube having a first region, a second region and a third region, the first region being proximal to the second region, the third region being distal to the second region, and the first region having an outer diameter greater than that of at least the second and third regions when the balloon is in the expanded configuration;
the proximal end region of the balloon engaged to the second region of the outer tube, at least a portion of the working region being disposed about and coextensive with at least a portion of the third region of the outer tube when the balloon is in the expanded configuration, and the outer tube first region being proximal to the proximal end region of the balloon, wherein the balloon comprises a folded portion that is proximal to the proximal annular end of the stent and distal to the distal end of the third region, the folded portion forming a bulge, the bulge abutting the proximal annular end of the stent when the balloon is in the unexpanded configuration;
the outer tube disposed about the inner tube, the inner tube extending along at least a portion of the first region, second region, and third region of the outer tube;
the outer tube comprises an outer neck, the outer neck comprising the second and third regions, the outer neck being substantially frustoconical in shape and the third region having a diameter greater than that of the second region.

2. The catheter of claim 1, wherein the distal end region of the balloon is engaged to the inner tube.

3. The catheter of claim 1, wherein the balloon further comprises a proximal waist having a diameter and the proximal end region comprises a proximal cone having a diameter, the proximal cone defining a region of the balloon distal to the proximal waist and proximal to the working region, the proximal cone, in the expanded configuration, having a tapered diameter increasing from a diameter substantially equal to the proximal waist diameter to a diameter substantially equal to the working region diameter.

4. The catheter of claim 3 further comprising a marker band positioned within the volume defined by a circumference of the third region.

5. The catheter of claim 4, wherein in the unexpanded configuration, the balloon disposed about the marker band has a greater diameter than the stent.

6. The catheter of claim 1 in which the outer tube comprises at least one opening extending completely through the material of the outer tube in at least one of the second region and the third region.

7. The catheter of claim 6 in which the at least one opening defines a shape, the shape selected from the list consisting of: rectangular, square, circular, elliptical, and irregular.

8. The catheter of claim 6 in which the at least one opening comprises a pair of openings, the pair of openings being diametrically opposed to one another across the outer tube.

9. The catheter of claim 1 further comprising a distal neck whereby:
   the distal neck has a distal end and a proximal end, wherein the distal neck is disposed about a portion of the inner tube and is distal to the third region of the outer tube, and the distal neck has a diameter smaller than at least a portion of the first region of the outer tube,
   the distal end region of the balloon is engaged to the distal neck, and
   at least a portion of the working region is disposed about the distal neck.

10. The catheter of claim 9 in which the stent further comprises a distal end and the balloon further comprises a distal fold, wherein a portion of the balloon is folded into a configuration having a smaller diameter than the distal neck and the crimped stent, the distal fold being proximal to the proximal end of the distal neck and distal to the distal end of the crimped stent.

11. The catheter of claim 9 in which the distal neck comprises at least one opening extending completely through the material of the distal neck.

12. The catheter of claim 11 in which the at least one opening extending completely through the material of the distal neck is positioned proximal to the distal end region of the balloon.

13. The catheter of claim 9 in which the distal neck is substantially frustoconical in shape.

\* \* \* \* \*